US005930461A

United States Patent [19]
Bernstein et al.

[11] Patent Number: 5,930,461
[45] Date of Patent: Jul. 27, 1999

[54] METHOD AND APPARATUS FOR AUTOMATED TISSUE ASSAY

[76] Inventors: Steven A. Bernstein, 2717 San Marcos Ave., Los Olivos, Calif. 93441; Page A. Erickson, 2505 Calle Montilla, Santa Barbara, Calif. 93109

[21] Appl. No.: 08/941,507

[22] Filed: Sep. 30, 1997

Related U.S. Application Data

[63] Continuation of application No. 08/218,143, Mar. 24, 1994, Pat. No. 5,675,715.

[51] Int. Cl.$^6$ ..................................................... G05B 13/00
[52] U.S. Cl. ................................................ 395/82; 395/99
[58] Field of Search ......................................... 395/99, 82

[56] References Cited

U.S. PATENT DOCUMENTS 5,355,439  10/1994  Bernstein et al. ......................... 395/82

OTHER PUBLICATIONS

S.A. Vere, "Planning in Time: Windows and Durations for Activities and Goals," IEEE Trans. on Pattern Analysis and Machine Intelligence, vol. PAMI–5, No. 3, pp. 246–267, May 1983.
P. Sjolund and M. Donath, "Robot Task Planning: Programming Using Interactive Computer Graphics," Proc. 13th ISIR, pp. 7–122 to 7–135, Dec. 1983.
S. Kawabe, et al., "Robot Task Planning System Based on Product Modeling," IEEE 1985 COMPINT—Computer Aided Technologies, pp. 471–476, Sep. 1985.
T.L. Isenhour, "Robotics in the Laboratory," J. Chem. Inf. Comput. Sci., 25, pp. 292–295, Dec. 1985.
N. Okino and M. Shono, "Robot Simulator in TIPS/Geometric Simulator," Robotics and Computer Integrated Manufacturing, vol. 3(4), pp. 429–437, Dec. 1987.
T.L. Isenhour and P.B. Harrington, "TORTS: An Expert System for Temporal Optimization of Robotic Procedures," J. Chem. Inf. Comput. Sci., 28, pp. 215–221, Dec. 1988.

I. Mazon, et al., "Automatic Planning of Pick and Place Operations in presence of uncertainties," IEEE Int'l. Workshop on Intelligent Robots and Systems, pp. 33–40, Dec. 1990.

W. Ko and S. Lee, "Robot Task Planning based on Resource Reasoning," Proc. 1991 IEEE Int'l. Conf. on Robotics and Automation, pp. 756–761, Dec. 1991.

*Primary Examiner*—Robert W. Downs
*Attorney, Agent, or Firm*—McDonnell Boehnen Hulbert & Berghoff

[57] ABSTRACT

A system which performs a plurality of independent analysis procedures simultaneously, possibly involving differing types of tissues and differing process steps, comprising a robotic arm, which may move the different tissue samples among a plurality of processing stations, and a processor, which may select the next tissue sample to move, when to move it, and where to move it to. The processor may direct the robotic arm to interleave the differing process steps. The processor may select a tissue sample to be moved in response to timing information about the procedures, which may specify the start time and end time of each process step. The specified times may be exact or may be a range of times. The processor may determine the exact time for a step by generating a possible sequence of steps and examining that sequence for conflicts, adjusting that sequence in response to those steps with a specified range of times, and iterating the calculation over a plurality of possible sequences. The processor may comprise a graphic interface by which an operator may specify the steps of a procedure. A display of grid locations may comprise symbols for the workstations, which an operator may identify with a pointing device such as a mouse. The operator may create a list of process steps for a procedure by selecting a sequence of workstations with the mouse, and associating timing or other information for each process step with the selected workstation. The operator may also choose to select a list of stored process steps for a procedure.

15 Claims, 8 Drawing Sheets

FIGURE 8

| Action | File | Edit | View | Calibrate | Setup | PROCESS LIST VIEW |
|--------|------|------|------|-----------|-------|-------------------|

| Step No. | Step Name | Min Time | Max Time | Yes/No/Hold |
|----------|-----------|----------|----------|-------------|
| 1 | buf | 00:00:15 | 00:05:00 | No |
| 2 | pad | 00:00:30 | 00:00:30 | Yes |
| 3 | buf | 00:00:15 | 00:05:00 | No |
| 4 | pad | 00:00:30 | 00:00:30 | No |
| 5 | buf | 00:00:15 | 00:05:00 | Yes |
| 6 | pad | 00:00:30 | 00:00:30 | Yes |
| 7 | block | 00:30:00 | 00:30:00 | Yes |
| 8 | pad | 00:00:15 | 00:00:30 | Yes |
| 9 | buf | 00:00:15 | 00:05:00 | Yes |
| 10 | pad | 00:00:30 | 00:00:30 | Hold |
| 11 | buf | 00:00:15 | 00:05:00 | Yes |
| 12 | pad | 00:00:30 | 00:00:30 | Yes |
| 13 | buf | 00:00:15 | 00:05:00 | Yes |
| 14 | pad | 00:00:30 | 00:00:30 | Yes |
| 15 | ab | 02:00:00 | 02:00:00 | Yes |
| 16 | pad | 00:00:30 | 00:00:30 | Hold |
| 17 | buf | 00:00:15 | 00:05:00 | Yes |
| 18 | pad | 00:00:30 | 00:00:30 | Yes |
| 19 | buf | 00:00:15 | 00:05:00 | Yes |
| 20 | pad | 00:00:15 | 00:05:00 | Yes |
| 21 | buf 2 | 00:00:15 | 00:05:00 | Yes |
| 22 | pad 2 | 00:45:00 | 00:45:00 | Yes |
| 23 | ab 2 | 00:00:30 | 00:00:30 | Yes |
| 24 | pad 2 | 00:00:15 | 00:05:00 | Yes |
| 25 | buf 2 | 00:00:15 | 00:05:00 | Yes |

METHOD AND APPARATUS FOR AUTOMATED TISSUE ASSAY

This application is a continuation of application Ser. No. 08/218,143 filed Mar. 24, 1994 now U.S. Pat. No. 5,675,715 issued Oct. 7, 1997.

BACKGROUND OF THE INVENTION

1. Field of the Invention

This invention relates to methods and apparatus useful in automated analysis or testing of tissue samples.

2. Description of Related Art

The analysis of tissue is a valuable diagnostic tool used by the pathologist to diagnose many illnesses and by the medical researcher to obtain information about a cell structure.

In order to obtain information from a tissue sample it is usually necessary to perform a number of preliminary operations to prepare the sample for analysis. There are many variations of the procedures to prepare tissue samples for testing. These variations may be considered refinements to adapt the process for individual tissues or because a particular technique is better suited to identify a specific chemical substance or enzyme within the tissue sample. However the basic preparation techniques are essentially the same.

Typically such operations might include the processing of the tissue by fixation, dehydration, infiltration and embedding; mounting of the tissue on a slide and then staining the sample; labeling of the tissue through the detection of various constituents; grid staining of tissue sections for analysis by an electron microscope or the growing of sample cells in culture dishes.

Depending on the analysis or testing to be done, a sample may have to undergo a number of preliminary steps or treatments or procedures before it is ready to be analyzed for its informational content. Typically the procedures are complex and time consuming, involving many tightly sequenced steps often utilizing expensive and toxic materials.

These procedures must usually be performed in a critical order for each sample and each treatment is frequently time dependent. Additionally the laboratory is often under extreme pressure to perform many different analysis as soon as possible, entailing many different procedures and tests.

A sample of tissue may undergo an optical microscopic examination so that the relationship of various cells to each other may be determined or abnormalities may be uncovered. The tissue sample must be an extremely thin strip of tissue so that light may be transmitted therethrough. The average thickness of the tissue sample or slice (often referred to as sections) is in the order of 2 to 8 micrometers (1 micrometer=1/1000th of a millimeter). A relatively soft and pliable tissue such as might come from an organ of the human body, in its fresh state can not be accurately cut into such thin sections. In addition, in order to see the individual constituents of the cells, such as the nucleus, the nucleolus, the cytoplasm and the cell membrane, it is preferable to have them colored by different dyes to produce a contrasting appearance between the elements. Very limited dye staining can be done on fresh or recently living tissue without resorting to chemical processing. Typically a sample of tissue 2.0 to 2.5 square centimeters in area and 3 to 4 millimeters thick is utilized. The tissue sample is then fixed in a material (a fixative) which not only preserves the cellular structure but also stops any further enzymic action which could result in the petrification or autolysis of the tissue. While many substances can function as a fixative, a four per cent formaldehyde or a ten per cent formalin solution is very common. Other common fixatives would include ethanol, picric acid or mercuric chloride usually with formalin. It should be remembered that in dealing with these substances the containers holding the materials must be suitable. For example mercuric chloride severely corrodes metals and therefor should normally be contained in a glass vessel.

To prepare good samples for microscopic examination the initial step should kill the enzymic processes of the tissue and should alter or denature the proteins of the cell through fixation. The period of fixation may take several hours or even a few days depending upon the tissue type, sample size and type of fixative being used.

After fixation, the tissue sample is often dehydrated by the removal of water from the sample through the use of increasing strengths of alcohol or of some other dehydrating fluid. Gradual dehydration is preferred because it causes less distortion to the sample than a rapid dehydration process.

The alcohol is then replaced by a chemical which mixes with wax or some other plastic substance which can permeate the tissue sample and give it a consistency suitable for the preparation of thin sections without disintegration or splitting. Fat solvents, such as chloroform or toluene are commonly used for this step. The sample, which has been dehydrated by the infiltration of alcohol, is next exposed to several changes of solvent over a period that may last from a few hours to days until the alcohol is completely replaced by the solvent. The sample is then exposed to a wax which is soluble in the solvent. If a paraffin type wax is used the infiltration is at a temperature above its melting point. After the wax infiltration the sample is allowed to cool and the wax solidify so that the sample is entirely embedded in and infiltrated by the wax.

A microtome is then utilized to cut thin slices from the tissue sample. The slices are on the order of 5 to 6 micrometers thick. The cut thin sections are floated on water to spread or flatten the section. The section is then disposed on a glass slide usually measuring about 8 by 2.5 millimeters.

The wax is then removed by exposing the sample to a solvent, the solvent removed by alcohol, and the alcohol removed by decreasing the alcoholic concentrations until eventually the tissue is once more infiltrated by water. The infiltration of the sample by water permits the staining of the cell constituents by water soluble dyes.

Prior to the development of automated procedures for the preparation of tissue samples, it often took from two to ten days before the tissue could be examined under a microscope. In more recent years automated processes have been developed utilizing apparatus to transfer the sample from one fluid to another at defined intervals, and as a result the preparation time has been significantly reduced to 24 to 36 hours.

Variations in the materials used in the preparation of the sample are advantageous under some circumstances. The use of ester wax allows sections 1 to 3 micrometers thick to be cut with less contraction than that which occurs when paraffin used. The sample is exposed to higher temperatures when paraffin wax is used. The use of cellulose nitrate embedding shrinks tissues less than wax, produces good cohesion between tissue layers and permits large undistorted sections to be cut 25 to 30 micrometers thick, if so desired. It is clear that persons with skill in the art of tissue preparation may use many different materials to which the samples may be exposed.

Tissue staining is a procedure which is utilized to make microscopic structures more visible. Perhaps the most common stain materials are haematoxylin and eosin. Haematoxylin is utilized to clearly stain the nuclei of cells dark blue. Eosin is used to stains the cell cytoplasm various shades of red or yellow, presenting a clear contrast to the blue stain of the nuclei.

Many synthetic dyes are derived from benzene which is colorless but by changing its chemical configuration color compounds are produced which are called chromophores. It is these chromophores which constitute the bulk of the different coloring dyes used in research and routine histology.

There are many techniques by which sample tissues may be stained and most of these techniques require exposing the sample to various solutions. Histochemistry is the science by which chemical reactions are used to identify particular substances in tissues. In addition, many enzymes can be detected by exposing a sample to a particular chemical substance on which the enzyme is known to have an effect such as turning the substance into a colored marker. Thus from the above it can be seen that a sample tissue may be exposed to various antibodies, enzyme labeled detection systems, colormetric substrates, counterstains, washing buffers and organic reagents.

Many experimental and observational research projects involve experimentation to authenticate new techniques and these experiments can be very extensive and time consuming.

In addition to the techniques that prepare samples for optical microscopy, techniques often must be utilized which make the use of electron microscopes suitable in the examination of tissue samples. Actually it has been found that the pathological examination of almost any disorder makes electron microscopy highly desirable and often essential.

Tissue samples for use with an electron microscope may be fixed in glutaraldehyde or osmium tetroxide rather than in the standard fixatives used for optical microscopy samples. Usually very small samples of tissue are embedded in methacrylate or epoxy resin and thin sections are cut (about 0.06 micrometers thick). Staining is most often done by colored solutions and not dyes and heavy metal salts are utilized to enhance contrasts of density.

From the above brief description of some of the techniques and materials used by a pathologist in the examination of tissues, it can be seen that for a research laboratory to carry out such a wide variety of processes and numerous different tests assisting apparatus would be desirable and almost mandatory.

Many pathology laboratories have in fact automated many of the simple and routine procedures described above such as simple staining or sample embedding. Where the same procedure is repeated with great frequency, laboratories have often designed specialized machines to perform the often repeated testing simultaneously on many samples. Typical of such machines are the equipment used in the routine analysis of blood samples. The equipment used in this type of laboratory is capable of treating multiple samples simultaneously to the same testing procedure, i.e., parallel testing or through the use of multiple machines the same result of parallel testing, is achieved. Alternatively the laboratory may perform the same test repetitively, i.e., sequentially and thus subsequent samples may be subject to a significant time delay.

Research laboratories often are required to perform non-routine analysis requiring many different test procedures. As a result of this lack of repetitive procedures, research laboratories have relatively little automated equipment to assist the researchers in their task. The most obvious season for this lack of automation is that the equipment presently available is dedicated to a limited number of procedures most commonly performed. The equipment is not flexible enough to permit a wide variety of operations to be easily accomplished nor does the present equipment permit easy and facile changes to the operations.

SUMMARY OF THE INVENTION

The invention provides a system which performs a plurality of independent analysis procedures simultaneously, possibly involving differing types of tissues and differing process steps. The system comprises a robotic arm, which may move the different tissue samples among a plurality of processing stations, and a processor, which may select the next tissue sample to move, when to move it, and where to move it to. In a preferred embodiment, the processor may direct the robotic arm to interleave the differing process steps, for example by time division multiplexing.

In a preferred embodiment, the processing stations may be disposed in a set of grid locations, so that the location of any one processing station may be specified by an X coordinate and a Y coordinate, and possibly a Z coordinate for height. The robotic device may comprise a bench robot with a rotatable tower, with sufficient degrees of freedom that it is able to reach each of the grid locations with suitable movement. The processing stations may comprise workstations for performing individual steps of the tissue assay procedures, such as solution trays, or other equipment useful in bioassay, biomedical or related environments.

In a preferred embodiment, the processor may select a tissue sample to be moved in response to timing information about the procedures, which may specify a time range (e.g., a minimum time and maximum time) each process step should take. The processor may determine the exact time for a step by generating a possible sequence of steps and examining that sequence for conflicts, adjusting that sequence in response to those steps with a specified range of times, and iterating the calculation over a plurality of possible sequences. The processor may also optimize the order in which samples are moved to minimize the total time required by the system to complete the procedures, for example by generating a plurality of possible sequences, evaluating each sequence for total expected time, and selecting the best sequence available.

In a preferred embodiment, the processor may comprise a graphic interface by which an operator may specify the steps of a procedure. A display of the grid locations may comprise symbols for the workstations, which an operator may identify with a pointing device such as a mouse. The operator may create or edit templates for workstations, create or edit lists of process steps for procedures, monitor the progress of ongoing procedures, or override the determination of what process steps to perform. For example, in a preferred embodiment, the operator may create a list of process steps for a procedure by selecting a sequence of workstations with the mouse, and associating timing or other information for each process step with the selected workstation. The operator may also choose to select a stored list of process steps for a procedure.

Thus, the invention provides apparatus and methods whereby a plurality of test procedures can be performed on several samples, e.g., through the use of time division multiplexing. The invention also provides apparatus for use in a laboratory for assisting in the performance of multiple tests which can be easily programmed by the operator to execute sequentially timed step procedures for a plurality of test samples. The invention also provides a flexible laboratory testing system which may use time division multiplexing to interleave the multiple steps of a plurality of test procedures to allow for a plurality of different procedures to be performed on several different test samples in parallel.

BRIEF DESCRIPTION OF THE DRAWINGS

FIG. 8 shows a process timing screen as viewed by an operator.

DESCRIPTION OF THE PREFERRED EMBODIMENT

In a preferred embodiment, a multiple axis bench top robot is located to reach peripheral auxiliary equipment disposed in the operational area of the robot. The robot may respond to the output of a PC type computer which utilizes process control programs and assay development software. Peripheral equipment, a plurality of work modules or workstations, is disposed in a grid like pattern around the bench top robot. The workstations may be disposed or arranged in any convenient pattern and may be represented by a template. Each grid location may contain the necessary equipment to perform a single step of a tissue assay procedure.

For example, a workstation at a grid position may contain a solution tray into which one or more slides may be immersed by the robotic equipment. The slide, or slides, could be immersed to a predetermined depth and retained in the solution tray for a precise time. It should be clear that each grid location may have a solution tray having different depths or different dimensions. Alternatively, a grid location could contain a slide holder or other peripheral equipment capable of performing a single function on the sample.

The robotic equipment or robotic arm may be controlled by a standard PC computer. The assay development software is graphic in nature and places a model of the peripheral grid on the screen of the computer. While each tissue assay may have all its steps preprogrammed the assay development software permits the steps of the procedure or the timing of the steps to be altered. The graphic nature of the presentation permits laboratory personnel to alter such elements without the necessity of relying on a computer or programming expert.

The process control software associated with the PC may monitor the progress of the assays, may permit manual override of the of an automatic operation, and most importantly, may permit scheduling of multiple assays simultaneously in parallel through the use of time interleaving of the various steps in the test procedures. Thus while sample one may be disposed at workstation in a grid location where it undergoes a drying operation, sample two may be located in a tray containing a staining solution while sample three is undergoing a fixation step. The timing of each step is accurate and the system interleaves the steps and utilizes the "waiting" or processing time between steps in a single procedure to perform operational steps on other samples which may be undergoing completely different preparation.

Laboratory Bench and Robotic Device

Figure 1:
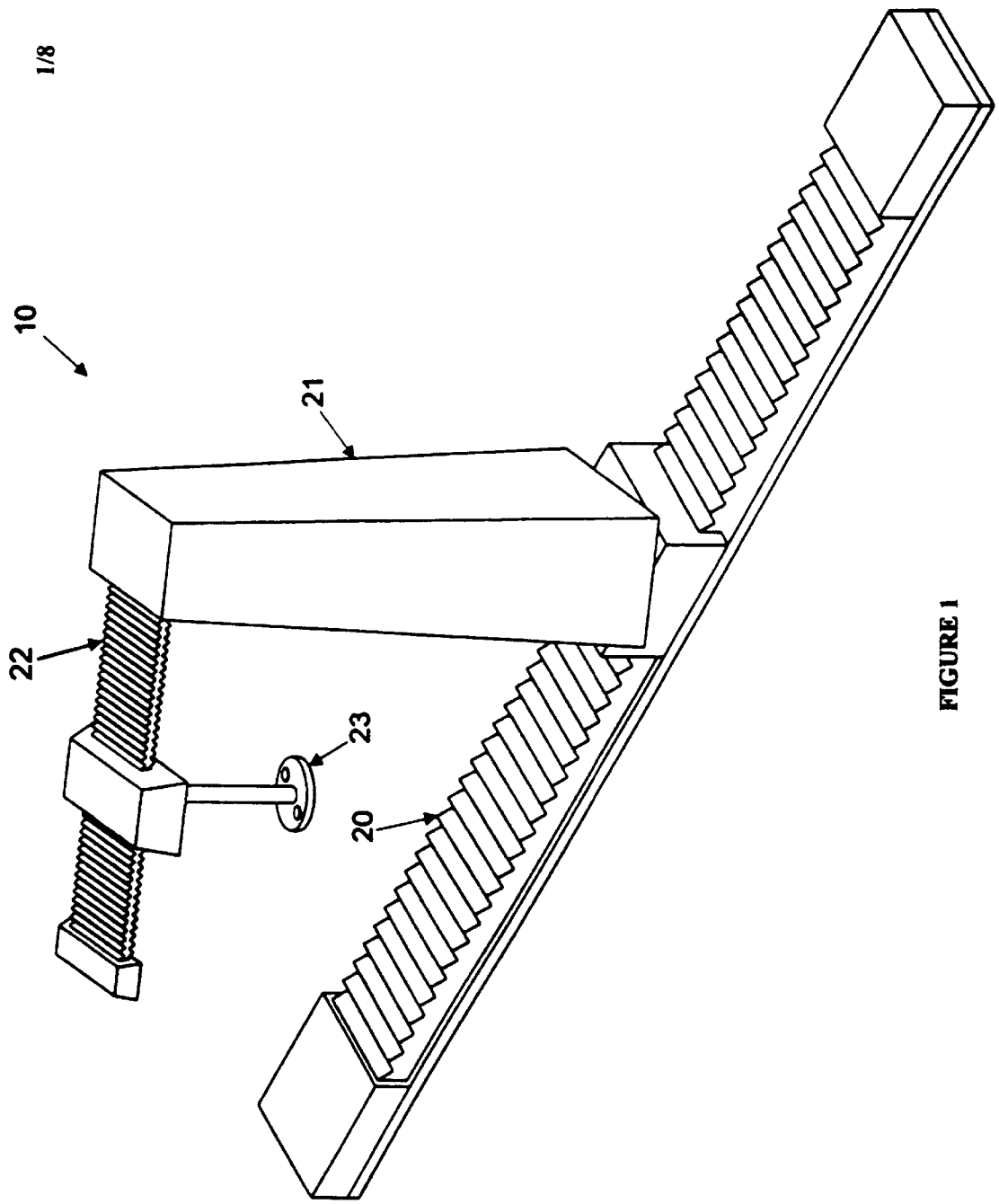
FIG. 1 shows a robotic device for use with the invention.
Figure 2:
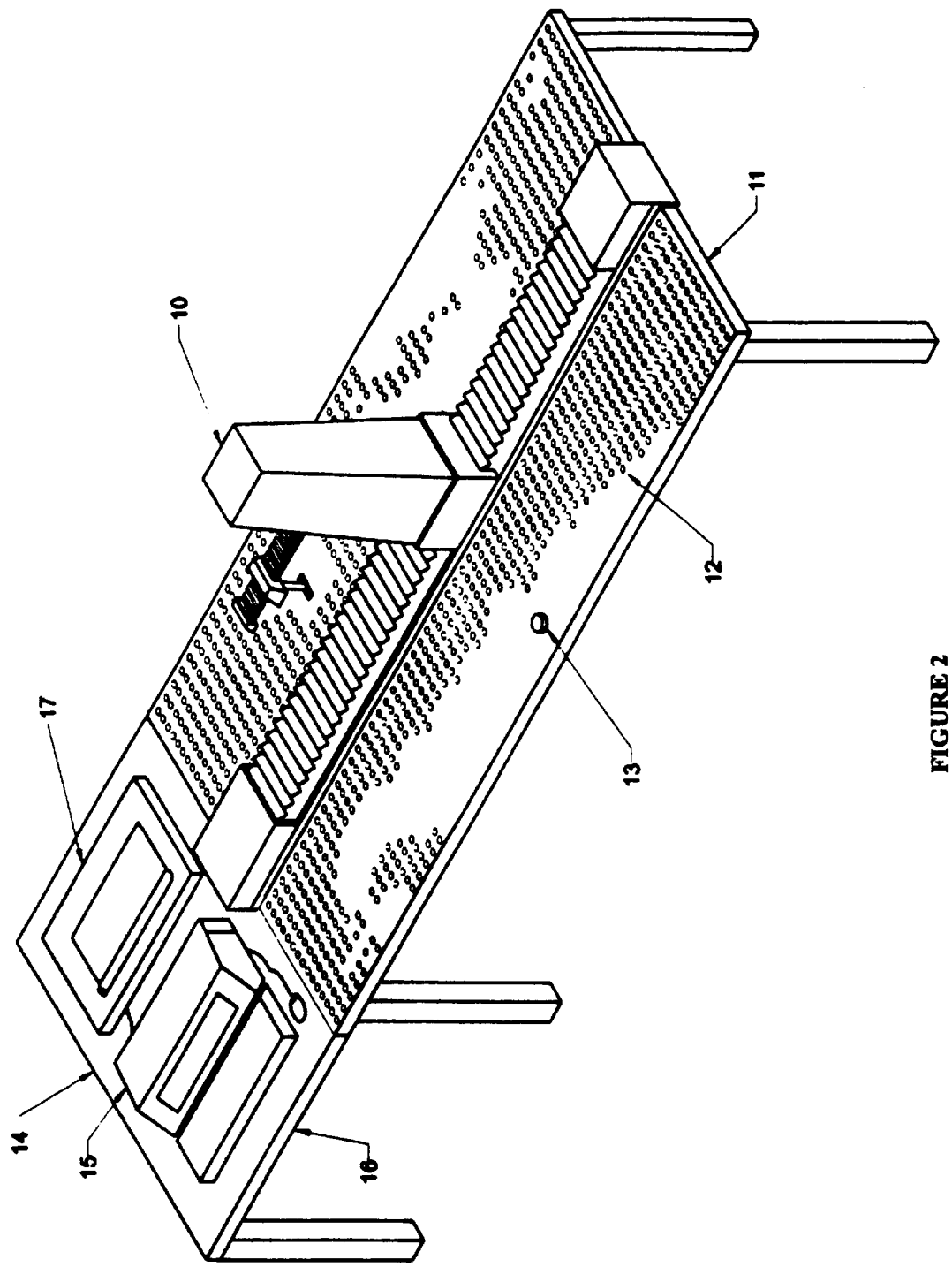
FIG. 2 shows a laboratory setup having robotic equipment like that shown in FIG. 1.
Figure 3:
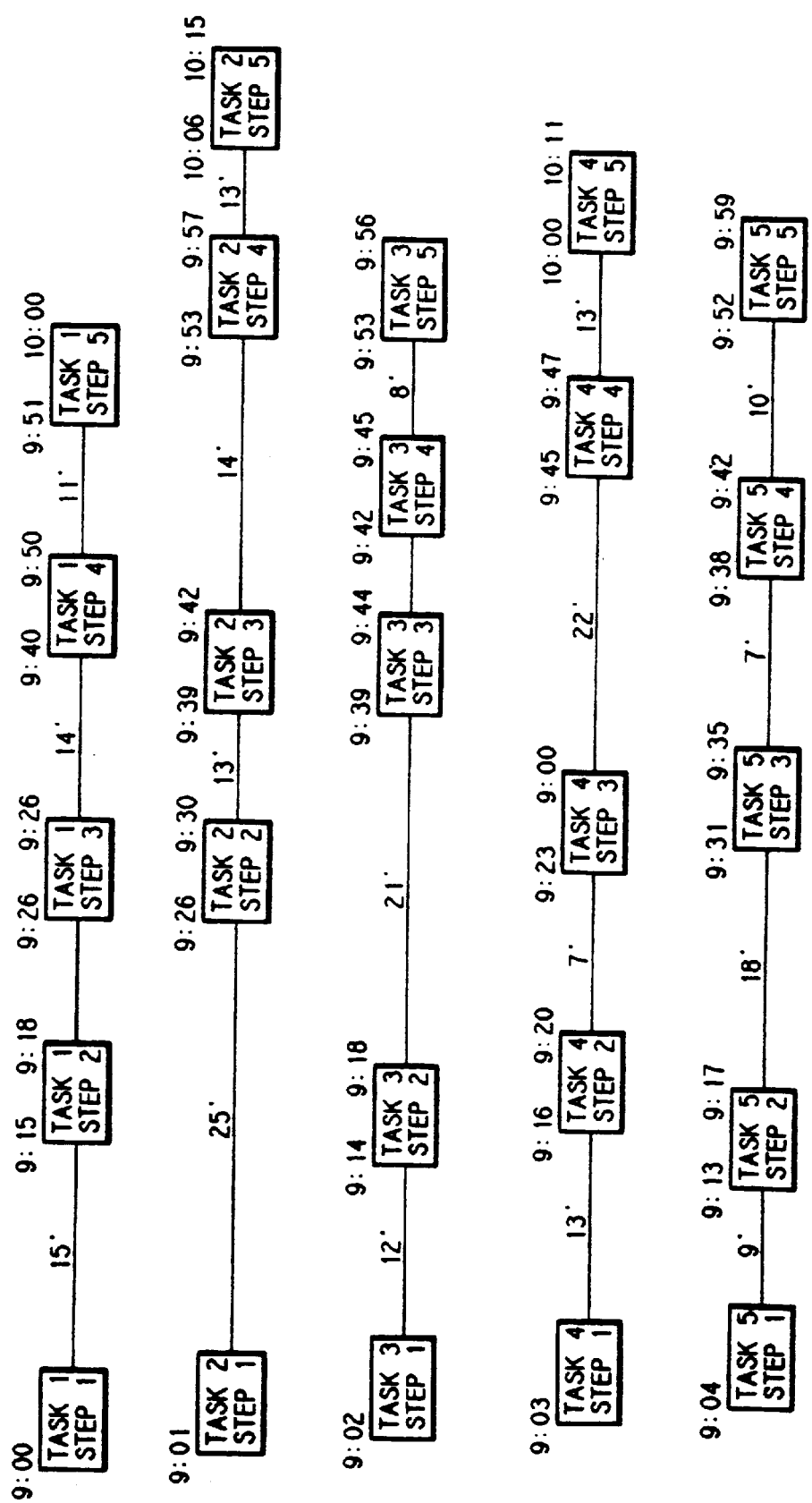
FIG. 3 is a flowchart showing a time line for five tasks.

FIG. 1 shows a robotic device for use with the invention. FIG. 2 shows a laboratory setup having robotic equipment like that shown in FIG. 1. The equipment may include a robotic device 10 mounted on a standard laboratory bench top 11. The bench top defines the operational area reachable by the robotic device 10. The bench top may have integral therewith a plurality of locating elements such as holes 12 Alternatively, the locating elements may be disposed on a separate base disposed between the robotic device 10 and the laboratory bench top 11. A template may be used to represent the operational area and to assist in defining the exact location of each workstation. Located on the bench top are one or more work modules 13. A control station 14 is located adjacent to the laboratory bench 11. The control station 14 may include a typical PC type computer 15, such as an IBM PC/2 or AT or any computer similar thereto, mounted on a desk 16 or other working surface. It would be clear to one of ordinary skill in the art, after perusal of the specification, drawings and claims herein, that other types of computers may be utilized to control the movement of the robotic arm 10. A printer 17 is shown although other peripheral equipments may be utilized in conjunction with the computer 15.

Referring to the bench top 11, a plurality of locating holes 12 are disposed at predetermined fixed locations relative to the robotic device 10. The locating holes are designed to receive modular workstations 13. Each modular workstation 13 is designed to be used in the performance of a particular process or step in one laboratory task or test procedure. Thus each function required to be performed in a task is associated with a work module 13 which has a predisposed known position on the work bench 11.

There exist in the prior art a number of methods by which the location of a particular work module 13 can be supplied to the computer 10. For example each work module 13 may include a floppy disk which would contain the physical characteristics of the work module, such as its height, width and length. The customized data for each module would be fed into the central processing unit of the computer and would query the operator, for example through a CRT display, to provide the location of the work module. The operator through the keyboard input would specify the location of the module on the locating grid. Thus for each work module or step of a task the computer would have stored in its memory the physical characteristics and location of the module.

In a preferred embodiment, the robotic device 10 is capable travel in an "X" direction along a lead screw 20. Disposed at right angle to and vertical with respect to the lead screw 20 is a second lead screw 21 which is capable of traversing lead screw 20. In addition, a gear or belt is capable of rotational movement relative to the lead screw 20. Coupled to the lead screw 21 is a lead screw 22 which is disposed at a right angle. A robotic hand 23 is mounted on lead screw 22 and is capable of rotation. The sample to be assayed (which may be a tissue sample) is mounted on the hand 23.

Thus the hand 23 on which the sample is mounted is capable of "X" movement along lead screw 20, "Y" movement along lead screw 21, and "Z" movement along lead screw 22. In addition, the lead screw 22 is rotatable and the hand 23 is rotatable. The system illustrated is capable of motion relative to five axes. Although the system is illustrated using lead screws 20, 21 and 22, it would be clear to one of ordinary skill in the art, after perusal of the specification, drawings and claims herein, that other robotic equipment could be provided that could decrease or increase the number of axes, that other techniques other than lead screws, (such as gears or belts or other devices) could be used, and that such other equipment or techniques would be workable, and are within the scope and spirit of the invention.

Typically, the range of movement along the "X" axis may be 72 inches, along the "Y" axis 12 inches, and along the "Z" axis 18 inches. Such a typical range of movement could provide approximately eighteen cubic feet of operational area.

System Operation

In order to illustrate the operation of this invention, let it be assumed that the laboratory has five example tasks to accomplish. For purposes of illustration, the five steps in each of the tasks will be utilized to demonstrate the multitasking capabilities of the invention. The five tasks and the five steps of each of the tasks are shown in Table 1 herein.

It is apparent from Table 1 that some of the tasks utilize the same steps such as Pad 1 or Buffer 1. If these steps were to be carried out in accordance with the principles of this invention, it would be necessary to provide only fourteen work modules even though twenty five steps were being performed. Disposed on the grid would be a separate work module for each of the fourteen different steps listed above. Thus there would be a Pad 1 module to be used in carrying out seven of the above steps. Alternatively, the user could provide multiple modules, each capable of performing the pad function. A Buffer 1 module would be used for five of the steps and a Buffer 2 module for two of the steps. Each of the remaining steps would have a module

TABLE 1

| Five Tasks | |
|---|---|
| Task #1 | Basic Fuchsin Staining |
| Step #1 | Buffer 1 |
| Step #2 | Buffer 2 |
| Step #3 | Basic Fuchsin |
| Step #4 | Pad 1 |
| Step #5 | Buffer 2 |
| Task #2 | Azure II & Methylene Blue Counterstaining |
| Step #1 | Azure II |
| Step #2 | Pad 1 |
| Step #3 | Buffer 1 |
| Step #4 | Pad 1 |
| Step #5 | Methylene Blue |
| Task #3 | Tissue Fixation |
| Step #1 | Isotonic Rinse |
| Step #2 | Primary Fixative |
| Step #3 | Buffer 1 |
| Step #4 | Buffer 2 |
| Step #5 | Secondary Fixative |
| Task #4 | Immunocytochemistry |
| Step #1 | Buffer 1 |

TABLE 1-continued

| Five Tasks | |
|---|---|
| Step #2 | Pad 1 |
| Step #3 | Blocking Antibody |
| Step #4 | Pad 1 |
| Step #5 | Buffer 1 |
| Task #5 | Slide Silinizing |
| Step #1 | APTES |
| Step #2 | Toluene |
| Step #3 | Water |
| Step #4 | Pad 1 |
| Step #5 | Oven | disposed on the grid to perform the necessary work associated with the step.

Figure 4:
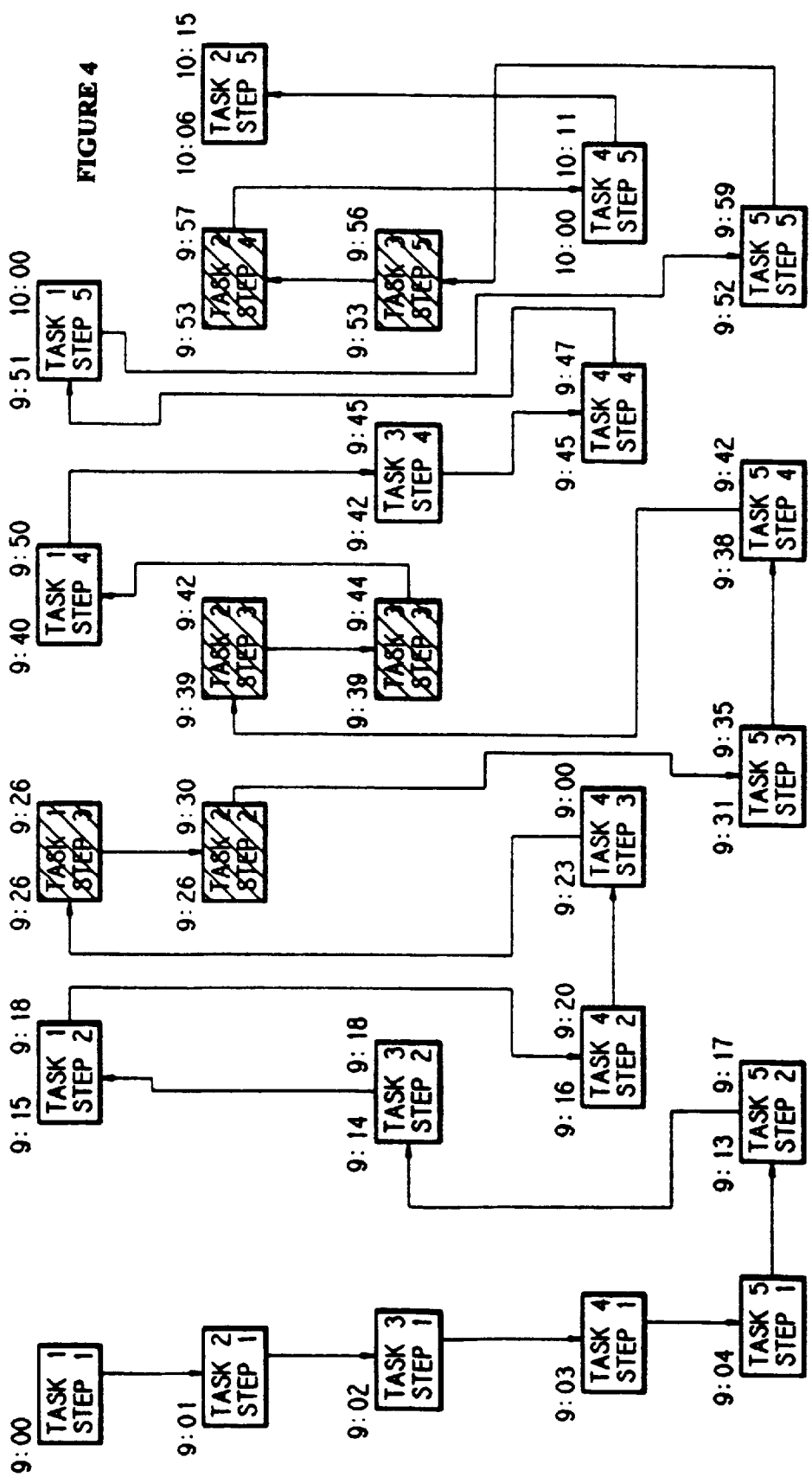
FIG. 4 is a flowchart illustrating multitasking of the tasks shown in FIG. 4.

It is often essential that the step of the task be performed within certain time limits. The timing of some steps can be critical. FIG. 4 is a flowchart showing a time line for the five steps of the tasks in Table 1. It should be noted that Task #1, Step #1 commences at 9:00 and has a duration of approximately fifteen minutes, inclusive of the time necessary to transport the sample to the location where Step #2 is performed. Thus Step #2 will commence at approximately 9:15. It should be noted that the timing for the start of Step #2 has some leeway in that it can commence between 9:15 and 9:18, providing leeway of three minutes. Step #2 has a duration of approximately eleven minutes and the sample is transported to the location where Step #3 will be performed. The time for performing Step #3 is critical as indicated by the lack of interval for the starting times. Step #3 must commence at 9:26. Fourteen minutes later the sample is undergoing Step #4, which can commence any time between 9:40 and 9:50. The last Step #5 is performed at 9:51. It should be noted that if each Step is commenced at the outer time limit Step #5 may not begin until 10:22.

In a similar manner it can be determined from FIG. 4 that the five steps of Task #2 may consume 1 hour and 34 minutes, Task #3, 1 hour and 9 minutes, Task #4, 1 hour and seventeen minutes and Task #5, 1 hour and sixteen minutes. Thus if the five steps of the tasks shown were to be performed sequentially the total time to completion would be six hours and thirty eight minutes.

Figure 5:
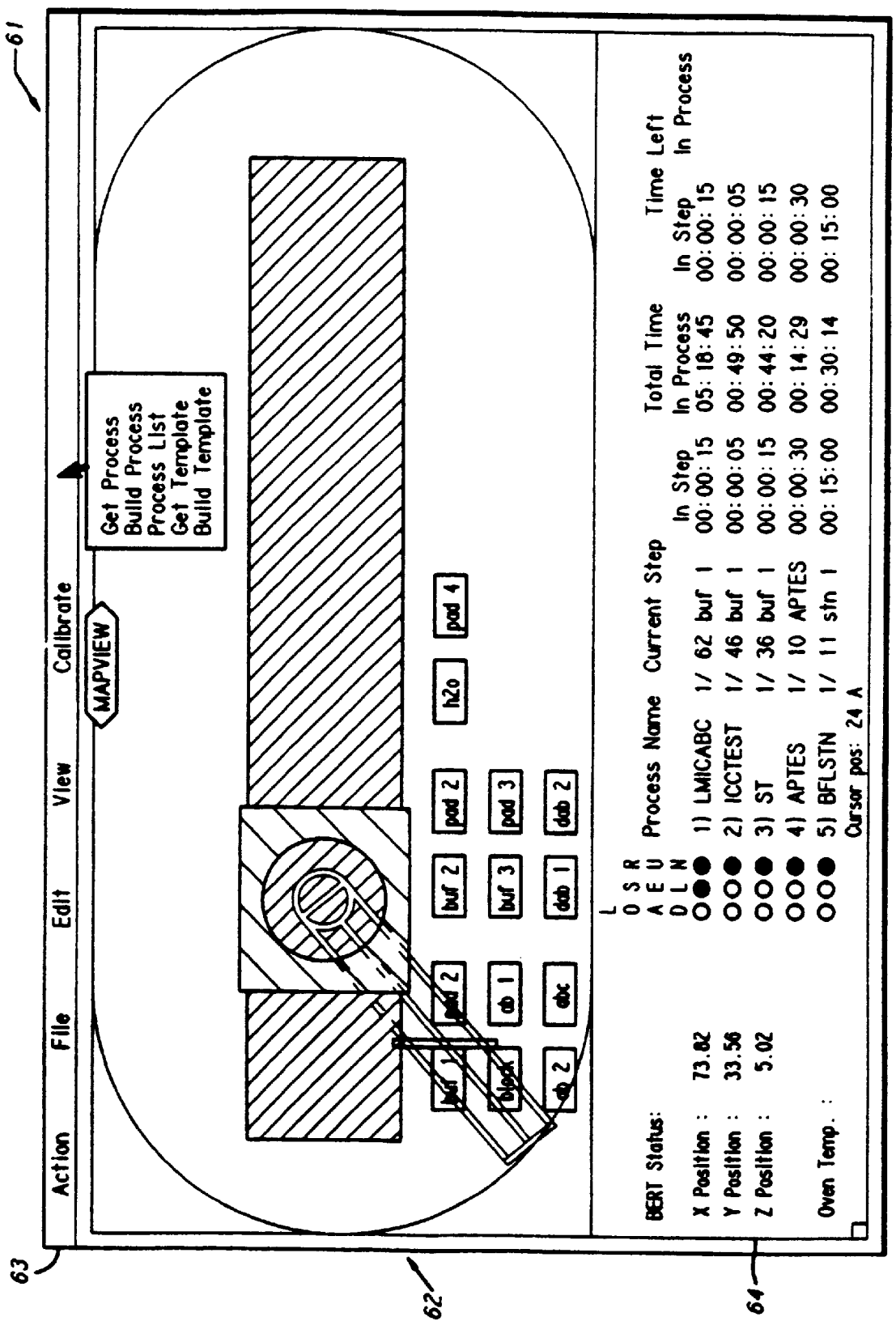
FIG. 5 shows a multitask monitoring screen as viewed by an operator.

Referring to FIG. 5, the multitasking method of this invention is therein illustrated to show the time interleaving of the steps of the multiple tasks. Assuming again for purposes of illustration and simplification of explanation that we are desirous of performing the same five steps for the same five tasks. Under the control of the computer the robotic hand would be commanded to obtain sample #1 or alternatively the sample could be brought to the robotic hand and for grasping. The hand retaining the grasped sample would move the sample to the location of the work module for Task #1, Step #1, i.e., Buffer 1. The sample would be freed from the hand and left at the work module. The hand would proceed to the location of sample #2 where it would grasp the sample and carry it to the work station where Task #2, Step #1 would be performed.

Each of the five samples would in turn be grasped by the robotic hand and transported to the work module associated with the first step of the task to be performed on each sample. It should be noted that the design of the Buffer and Pad work modules permit the simultaneous treatment of at least two samples from different tasks. Alternatively, two work modules could be provided so that each sample could be treated in a different module.

After locating sample #5 in the Task #5, Step #1 module, the robotic hand returns to the module for Task #5, Step #1 and gasps the sample #5 and transports it to the module for Task #5, Step #2. Following the path illustrated in FIG. 5, the hand proceeds from the Task #5, Step #2 module to Task #3, Step #3 module where it grasps sample #3 and transports it to Task #3, Step #2 module where the sample is deposited. The hand then returns to the location of the first sample which is in the module associated with Task #1, Step #1 and takes it to the module for Task #1, Step #2. The hand returns to the location sample #4 and carries it to Task #4, Step #2 and then at the appropriate time transports the same sample to Step #3 of Task #4.

At this point in the operation of the system, the computer detects that Task #1, Step #3 and Task #2, Step #2 are both scheduled to start at the same time, 9:26. In order to resolve the conflict the system utilizes a technique, herein termed "fuzzy timing", to process the control of the robotic hand and optimize the process. Fuzzy timing may comprise the window of time during which each process (Task) step may occur without affecting the process results. Some steps of a process may be critically timed, i.e., the time required for that step is exact, such as Task #1, Step #3 in FIG. 5, but in general most steps a process the timing is less critical and may comprise any amount of time within a known range and thus are noncritical in their timing, such as Task #2, Step #2, which has a window of 4 minutes, as shown in FIG. 5. The system of this invention uses these windows of time to advantage as to optimize (minimize) the time necessary to complete the multiple tasks.

The use and advantages of "fuzzy timing" can be illustrated by considering two different tasks, each having a process step terminating at the same time or within moments of the another. Assuming that both steps are critically timed in so far as the termination time is concerned, it is apparent that both samples from the two different steps can not be moved to the next step in each process simultaneously since concurrent movement of two samples is not within the capabilities of this embodiment. Thus it is necessary to adjust the starting times for the two steps relative to each other so that the ending times will allow for the movement of each sample to its next process step. While this can be done quite easily, it is clear that the mere adjustment of a starting time for a step in the process may well cause other timing conflicts. It is possible that under such conditions the system could not support simultaneous throughput of multiple processes unless the timing was altered.

Fuzzy timing allows the system additional flexibility since by providing a window of time at each noncritically timed process step, conflicts will be minimized through the adjustment of timing at the step level, rather than by shifting the timing of the whole process or task.

System Control by Operator

In order to use the system of this invention the operator (which might be a human user or a control processor) may first determine the processes that are to be carried out the apparatus. Each step of each process may be defined. To assist the user an index of work stations may be provided to allow the user to determine which process steps can be employed. Alternatively, each work station can be represented by an icon on the CRT display and a help index made available that the user may determine the capabilities of each work station by referring to the icon and its associated help screen.

As previously described with reference to FIGS. 1–2, the apparatus of the invention uses a locating grid or template presenting the operational work area reachable by the robotic device 10 in which the work station locations may be defined. Each position on the grid is accurately determined and can be imparted to the computer to provide certainty of location. The exact relative position of each work station may be stored in the control system. The use of the predetermined grid locations permits the user of this system to have the freedom of designing individual templates to match the user's need and to design the steps of a process to provide relative limited ability in creating processes, limited only by the available work stations.

Figure 6:
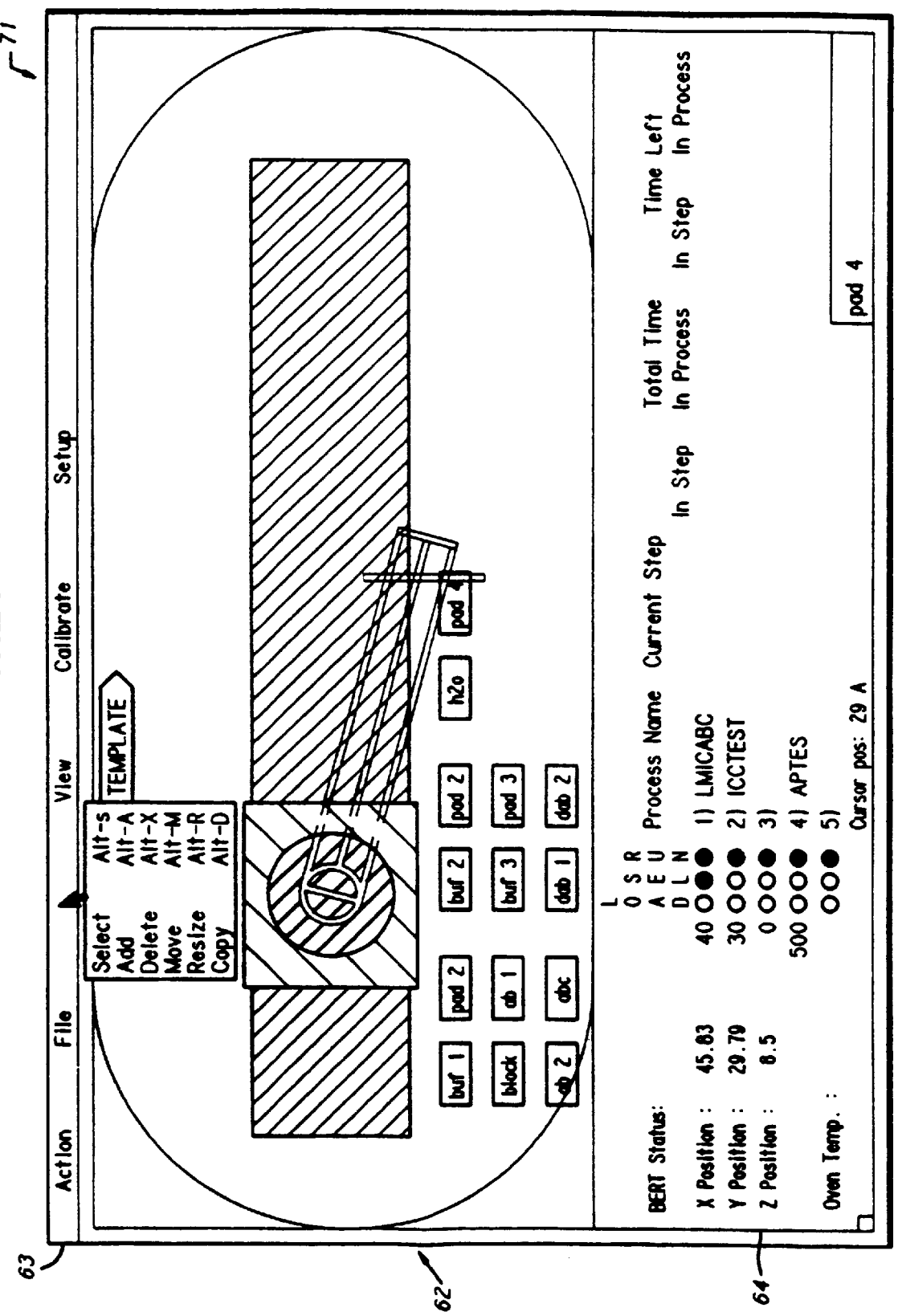
FIG. 6 shows a template building screen as viewed by an operator.
Figure 7:
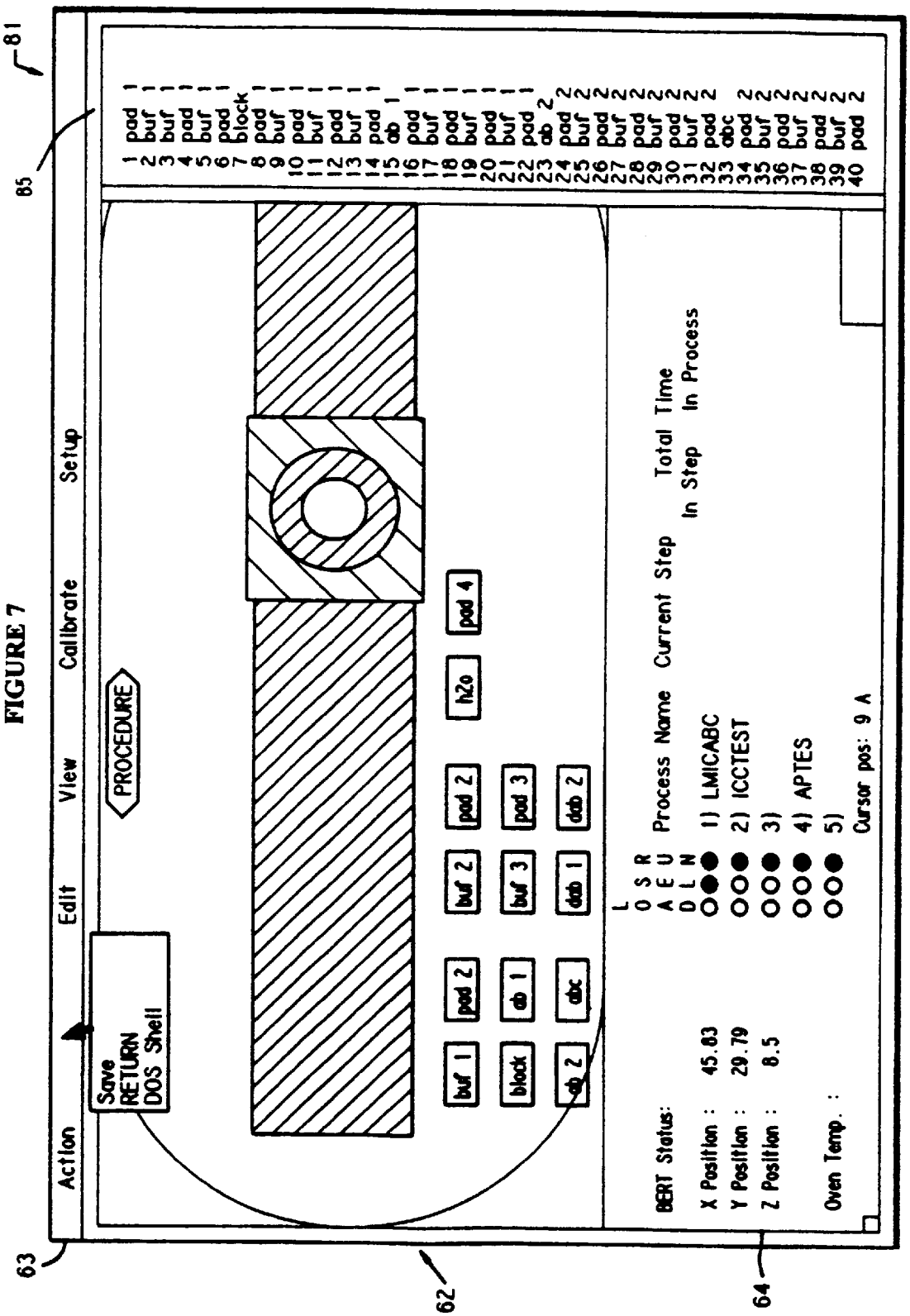
FIG. 7 shows a process building screen as viewed by an operator.

A graphic replica of the grid in which the work stations located is provided on the screen of the computer, such as shown in FIGS. 6–8. Included in this graphic is the robotic arm position. In order to quickly input the steps of a process to the computer (1) a template builder and (2) a process builder have been created to interact with graphic replica of the work area. These two tools, template builder and process builder, allow the user to design a new process or modify an old process, easily and quickly without the need to have knowledge of computer programming. Through the use of a keyboard or mouse, the two builder tools are rendered interactive with the user.

A work station grid area may typically have holes disposed on one inch centers, or any other predetermined pattern. As is usual the columns of holes may be identified by letters while the rows of locating holes may be identified by numbers. Thus each hole can be uniquely identified by a letter-number combination.

Work station units or peripherals have been designed which have elements which cooperate with the grid locating holes and thus facilitate the exact location of each station. When located on the grid each work station will have a unique describer positively identifying its location.

Thus the user may commence operating the system by viewing a graphic representation of the work area surrounded by icons representing various work stations. As will be described below the user can quickly design a new template if so desired. Alternatively, the template may be called up from a disk by the computer.

The steps of the process are communicated to the computer through the use of an interactive peripheral such as a mouse. The operator locates the mouse cursor on the icon representing the first step of the process and drags the icon to the desired location. Thus by pointing and clicking the mouse the work stations necessary to accomplish the steps of the process are disposed on the graphic grid. It is of course desireable that the physical workstations be located on the grid in the locations shown on the display. Alternatively, the location of the work station can be fed into the computer in other ways, such as through the keyboard or even by locating the physical work station on the grid with feedback to the computer identifying the work station and location.

Thus an unsophisticated user has the ability to design processes quickly imparting great flexibility to this apparatus. It should of course be recognized that this information can be stored on a disk and the apparatus set up accomplished by reading the information off a disk into the memory of the computer.

In creating the template the operator uses a mouse to draw replicas of each station on the screen, such as shown in FIG. 7, a template building screen. Each station is given a unique identification which may be a name, symbol or code. The dimensions of the station may be drawn on the screen and in particular it is essential that the height of the work station is recorded. The position, identification, height and other dimensional criteria are stored in the RAM memory of the computer CPU. When the template is completed it may be stored to disk as a template file, to be recalled as needed.

As is not unusual in the operation of computers, provisions are made to add, delete, move, resize or duplicate any of the stations. Any available template previously stored may be recalled to be used or to assist in the creation of new templates. Of course the apparatus may have the ability to enable the operator to print out a graphic replica of the screen and a list of station positions, identifications, heights or other dimensions.

Once the template is complete the operator may use the stations of the template to create a process, step by step.

The process builder, like the template builder, uses a graphic replica of the workstation area on the computer screen, such as shown in FIG. 8, a process building screen. One of the templates previously created by the template tool builder described above, is recalled from memory and displayed on the screen together with the work area. The screen cursor is moved to the desired station icon and the particular station is selected. This procedure may utilize a mouse and a point and click procedure.

Each station of the process is selected in sequence and the station is then added to a list denoting the steps of the process in sequential order. The robotic device would ultimately be controlled to move to each of these stations in the order in which they were added the process list. Since the characteristics of each work station were previously stored in the computer, the robotic device would be programmed for the proper movement. For example, the height of each station was previously stored in the memory, and if the robotic arm were to traverse the area in which a high work station was located, it would be instructed to elevate the hand so that any sample mounted thereon would clear the high work station. It is also possible to design the operational area to have clear paths or lanes defining travel routes for the robotic device 10. In any event, the movement of the robotic device among the workstations may be designed to be free of collisions based upon recognition of the entity, position and geometry of the work stations. As will appreciated as the number of work stations increase the amount of information that should be considered in order to avoid collisions and otherwise avoid conflicts in instructions also increases.

Following the graphic design of the steps of the process, the process list would be called up on the screen and the procedure for each step would be imparted, such as shown in FIG. 9. This procedure would essentially indicate a range of time each sample should remain at each station. For each step a minimum time and a maximum time for the sample to remain at the work station would be recorded. As noted herein, the minimum time may be specified to be zero, and the maximum time may be specified to be infinity. The times for each station, except where the timing is critical, would allow the system a timing window which can be used to avoid timing conflicts between different steps of separate tasks and thus maximize the multitasking capabilities of the apparatus.

Pseudocode for Designing or Running New Processes

The method carried out by the control station 14 for template building and process building may be described by pseudocode shown in Tables 2–3 herein, respectively. It would be clear to one of ordinary skill in the art, after perusal of the specification, drawings and claims herein, that modification of known processor systems to perform the functions disclosed in this pseudocode (as well as in other pseudocode disclosed herein) would be a straightforward task and would not require undue experimentation.

TABLE 2

| Template Builder |
|---|
| procedure template_tool(); |
| set up screen; |
| draw robot replica graphic; |
| draw grid; |
| display mouse cursor; |
| select template design tool; |
| while (not finished) |
|     select tool; |
|     case (edit tool) |
|         add:     draw new station on screen via mouse by dragging mouse away from start point while having mouse button 1 depressed; |
|                 update screen with a rectangle being displayed along cursor displacement; |
|                 enter id via keyboard; |
|                 position height of station; |
|                 store position and id; |
|         select:     move cursor to station via mouse; |
|                 click mouse to select; |
|                 selected station changes color to show it is selected; |
|         delete:     click mouse button 1 to delete; |
|         move:     place move crosshair on selected station; |
|                 place cursor on crosshair; |
|                 press mouse button 1 down and drag station to new position; |
|                 screen update after each new grid position move; |
|         resize:     place resize crosshair on selected station; |
|                 place cursor on crosshair; |
|                 press mouse button 1 down and drag station to new size; |
|                 screen update after each new size; |
|         duplicate:     get current selected station position, size and height information; |
|                 offset duplicate to new position; |
|                 add id; |
|                 store new station position and id; |
|     case (edit tool) end; |

TABLE 2-continued

Template Builder

```
case (file tool)
        get template:    display list of template files;
                         select via mouse cursor;
                         open selected template;
                         display template stations on screen;
                         hold station records in RAM;
        save template:   display list of template files;
                         select via cursor or enter new name via keyboard;
                         store template file to disk;
        case (file tool) end;
end (template_tool);
```

After the station sequence has been entered and the times for each step recorded, the process may be stored to disk

TABLE 3

Process Builder

```
procedure process_tool();
set up screen;
draw robot replica graphic;
draw grid;
draw process list;
display mouse cursor;
        case (file tool)
                get template:     display list of template files;
                                  select via mouse cursor;
                                  open selected template;
                                  display template stations on screen;
                                  hold station record in RAM;
                get process:      display list of process files;
                                  select via mouse cursor;
                                  open selected process;
                                  display process list in list window;
                                  display associate template stations on the screen;
                                  hold process station records in RAM;
                save process:     display list of process files;
                                  select via cursor or enter new name via keyboard;
                                  store process file to disk;
                case (file tool) end;
        case (select_tool):
                if cursor in work station area and on a station and mouse
                button 1 down then add station to process list;
                if cursor in process list and on list member and mouse button
                1 down then delete from list;
                case (select_tool) end;
        case (window select)
                Process List:     (1) set up screen;
                                  (2) display process in list mode;
                                  (3) enter min/max time via keyboard;
                                  (4) scroll down screen;
                                  (5) do steps 3-4 until finished;
                                  (6) exit back to previous window;
                Run/Control:      return to Run/Control window;
end (process tool);
``` as a process file. The process file may be loaded in the future and the apparatus used to run the same process at a later date. Of course the template file may be linked to the process file so that when a process is called up from storage and run on the computer the template files used in the process may be automatically called up and displayed on the computer screen.

The procedure list on which the times at each step were recorded may be called up at any time and for the stations still not used by the robotic device, adjustments to the timing could be made provided that the steps in the process which are to have their timing altered have not been reached. Thus the operator can adjust the timing of the steps even as the process is running.

Visual Operator Interface

FIG. 6 shows a multitask monitoring screen 61 as viewed by an operator. A multitask monitoring screen 61 may be shown on a display device coupled to the computer 15, such as a display monitor. The multitask monitoring screen 61 may comprise a display section 62, a menu section 63, and a status section 64.

The display section 62 may show a representation of the robotic device 10, bench top 11, holes 12, work modules 13, and related equipment. For example, the display section 62 may show positions for workstations 13 for a selected process.

The menu section 63 may show command options and suboptions which are available to the operator and may allow the operator to select one or more command options and suboptions. For example, the menu section 63 may have a menu with the command options "GET PROCESS", "BUILD PROCESS", "PROCESS LIST", "GET TEMPLATE" and "BUILD TEMPLATE". The operator may display available command options and select one or more command options in the menu section 63, by means of a pointing device, such as a mouse, as is well known in the art.

The status section 64 may show a set of status information about processes. For example, the status section 64 may show five processes which are in progress, and may show for each process the current step it is on, the total time it has taken (both for the current step and for the entire process), and the time remaining that it will take (both for the current step and for the entire process). Note that elapsed time for the current step may be zero because the robotic device 11 might wait for the proper time before depositing the sample in the workstation 13 for that process step, e.g., holding the sample in the robotic hand 23 if travel from a prior step took less time than expected. The status section 64 may also show the X, Y and Z position of the robotic arm.

FIG. 7 shows a template building screen 71 as viewed by an operator. A template building screen 71 may be shown on a display device coupled to the computer 15, such as a display monitor, in like manner as the multitask monitoring screen 61. The template building screen 71 may comprise a display section 62, a menu section 63, and a status section 64, in like manner as the multitask monitoring screen 61.

When using the template building tool, described herein, the operator may view the template building screen 71 and manipulate the commands and elements thereon by means of a pointing device, such as a mouse. A detailed description of how the operator may use the template builder tool is given herein.

FIG. 8 shows a process building screen 81 as viewed by an operator. A process building screen 81 may be shown on a display device coupled to the computer 15, such as a display monitor, in like manner as the multitask monitoring screen 61. The process building screen 71 may comprise a display section 62, a menu section 63, and a status section 64, in like manner as the multitask monitoring screen 61, and a workstation section 85.

The workstation section 85 may show a set of names or other identifiers of workstations 13. The operator may select one or more workstations 13 for inclusion in a process, by means of a pointing device, such as a mouse.

When using the process building tool, described herein, the operator may view the process building screen 81 and manipulate the commands and elements thereon by means of a pointing device, such as a mouse. A detailed description of how the operator may use the process builder tool is given herein.

FIG. 9 shows a process timing screen 91 as viewed by an operator. A process timing screen 91 may be shown on a display device coupled to the computer 15, such as a display monitor, in like manner as the multitask monitoring screen 61. The process timing screen 91 may comprise a plurality of lines 92, each of which may have an identifier section 93, a name/descriptor section 94, a minimum time section 95 and a maximum time section 96.

When using the process building tool, described herein, the operator may view the process timing screen 91 and enter minimum times (in the minimum time section 95) and maximum times (in the maximum time section 96) for each process step at each line 92. Each process step may thus have a line 92 with an identifier in the identifier section 93 and a name or descriptor in the name/descriptor section 94.

The minimum time section 95 for a line 92 may specify a minimum time which the designated process step may take, which might be zero. If the minimum time is zero, additional data may be noted to indicate whether the designated process step may take a single tick of a timing clock for the robotic device 10, or if the designated process step may be skipped entirely.

The maximum time section 96 for a line 92 may specify a maximum time which the designated process step may take, which might be infinity. If the maximum time is infinity, the system may delay completion of the designated process step until after all other process steps with finite maximum time have been completed.

Each line 92 may also have an additional data section 97 for the designated process step, which may specify whether (1) the step is to be done, (2) the step is to be skipped, or (3) the process is to be "held" or temporarily halted at the designated process step for input from the operator. In the latter case, for example, the process might be "held" at the designated process step until an operator confirms that the process should continue.

Multitasking and Optimization

Having delineated all the steps of all the procedures, the computer may determine the most efficient manner for carrying out the procedure. The task would be simple if the steps of the first process were to be completed before the apparatus started on the second process. Through the use of time interleaving, multiplexing or multitasking the computer is utilized to keep track of multiple operations so as to perform a number of different processes each having a multiplicity of steps simultaneously.

In multitasking, a number of samples, each undergoing separate exposures may all be worked on simultaneously. In time interleaving, the robotic arm may operate through a sequence which is determined by the timing of the individual steps of many processes and the robotic arm transports different samples in a time efficient sequence rather than a process ordered sequence. Although the robotic device can only move one sample to a work station at a time, the entire system is continuously monitoring, scheduling and processing all tasks and their times at each station concurrently. At each step the process performed at that workstation continues (e.g., chemical reactions) even when the robotic arm is not currently attending to it. In other words, the sample is disposed in the workstation and the robotic arm continues to grasp another sample. The process step continues to work on the first sample while the robotic arm is attending or transporting the second sample. The multiple process steps that are being done, one to each sample, are being done in parallel and are not serial processes.

In fact the robotic arm works on a sample for a short period of time during which it usually transports a sample to a work station and then leaves that sample and works on another sample or samples before returning again to the first sample. Thus the robotic device work on each sample is suspended during the time interval that it is working on another sample or during which the samples are being processed at a work station.

The multitasking of the different processes is dependent upon the instructions issued to the robotic device, relative to the timing of each of the steps in the multiple processes and the optimization of the multitasking operations, to move the samples at the scheduled times determined by the computer inputs.

The computer control (software) may first determine all the robotic movements necessary to complete the entire run of all the steps in all the processes to be run. This determination may be completed before any movement is initiated. If at any time during the running of the multitasking any steps are added to one or more of the processes or any of the steps are reconfigured during the run, a new determination may be completed wherein the computer recalculates all the movements necessary to complete the run and insures that there is no time interference created by the modification to the run. This method of predetermining the movements can of course be replaced by a real time method of determining movement but it is believed that the predetermining method is more advantageous. The predetermining method identifies time conflicts, if any, where the robotic device would be required to perform two tasks simultaneously, resolves any such conflicts that may exist, and optimizes the schedule for the minimum time required to complete the entire run of the multiple processes.

This method of predetermination employs certain decision making procedures which are designed to permit the computer to resolve time conflicts and iteratively optimize the schedule. An iterative optimization method is used because the complexity of scheduling different multiple tasks, each with the possibility of having multiple critically timed steps, is too complex to be solved by using mathematical techniques. In addition, the decision making rules allow the resolution of other conflicting requirements for other resources such as the peripheral equipment or work station modules, which may be used in conjunction with the robotic equipment.

As described above, a predetermined schedule may be developed to resolve time and resource conflicts and the schedule may be iteratively optimized to minimize the time required to complete the steps of the multiple processes. In order to interleave the steps of the multiple processes each step of each task is examined at predetermined intervals, e.g., one minute. A calculation is made of the time to completion of the current step. If the step incubation time is finished a move condition results. If that is the only move condition during this time, i.e., only one move condition occurs, the robotic device will be scheduled to move to the next step in accordance with the predetermined schedule. However, if more than one sample is scheduled to move time arbitration ensues. Time arbitration determines the fuzzy time window for each of the time conflicting steps and selects the sample in the most time critical step to move. If more than one step has a critical time, the computer compares the times during the previous movement and varies the timing of the previous tasks to resolve or prevent bottlenecks from occurring. In a similar manner a single resource can be scheduled to work on two different samples during the same time period and such conflicts can be resolved in a similar manner using the arbitration method.

Pseudocode for Multitasking

The method carried out by the control station 14 for multitasking may be described by pseudocode shown in Tables 4–8 herein. It would be clear to one of ordinary skill in the art, after perusal of the specification, drawings and claims herein, that modification of known processor systems to perform the functions disclosed in this pseudocode (as well as in other pseudocode disclosed herein) would be a straightforward task and would not require undue experimentation.

TABLE 4

Multitasking Data Structure

```
STRUCTURE TASK ARRAY [ 1500 elements ]
BYTE            PROCESS NUMBER;
BYTE            TASK NUMBER;
CHAR [25]       TASK NAME;
INTEGER         TASK X COORDINATE OF WORKSTATION;
INTEGER         TASK Y COORDINATE OF WORKSTATION;
LONG INTEGER    ENCODED REAL TIME FOR PICKUP OR DROPOFF;
CHAR [1]        DROPOFF/PICKUP FLAG;
CHAR [5]        MOVE_FLAG;
                { When TRUE the process flagged needs to move to next task in
                progress. This information is entered into the task array. If multiple
                flags are set simultaneously the process steps must be arbitrated. }
CHAR [5]            RESOURCE_FLAG;
                { If set TRUE, two or more tasks require the same resource.
                Resource arbitration is done to resolve all conflicts. }
```

TABLE 5

Multitasking (Build Schedule)

```
PROCEDURE BUILD_MULTITASK_SCHEDULE ()
    { This routine is called a number of times with different seeding to build a statistical
    sampling of a number of schedules. The calling routine picks the most optimul schedule to
    run. }
BEGIN
    { Initialize timer and pick a process for first move. For iterative tasks, processes will be
    started in various orders to seed task builder and establish different scheduling. At each
    timer tick all processes are examined to check whether it is time to move to next position.
    If TRUE the task will be entered into the task array at the scheduled time. If more than one
    process needs movement at the same timer tick, time arbitration ensues. If two or more
    processes need the same resource, resource arbitration is undergone. This process continues
    until all tasks in all processes are complete. }
```

TABLE 5-continued

Multitasking (Build Schedule)

```
    TIMER = 0;
    START_FIRST_PROCESS;
    WHILE NOT ALL PROCESSES STARTED DO BEGIN
        INCREMENT TIMER BY 1;
        IF ANY TASK NEEDS MOVEMENT THEN
            SET TASK MOVE FLAG
            ELSE
            START_NEXT_PROCESS;
        IF MOVE_FLAG > 1 THEN TIME_ARBITRATE ();                    { check for multiple moves }
        IF TASK_MOVE THEN ADD TASK TO TASK_ARRAY [TASK_COUNTER]
    END;
    WHILE NOT ALL PROCESSES COMPLETED DO BEGIN
        INCREMENT TIMER BY 1;
        IF ANY PROCESS NEEDS MOVEMENT THEN SET TASK MOVE FLAG;
        IF MOVE_FLAG > 1 THEN TIME_ARBITRATE ();                    { check for multiple moves }
        IF TASK_MOVE THEN ADD TASK_ARRAY [TASK];                    { check for resource use }
    END;
END;
```

TABLE 6

Multitasking (Time Arbitrate)

```
PROCEDURE TIME_ARBITRATE ()
    { If two or more processes must be moved simultaneously, the times are arbitrated, first by
    examining fuzzy time range and adjusting those process tasks with fuzzy time. If the
    colliding processes are critically timed the processes' prior tasks are rearranged to
    circumvent the collision. This procedure is called in REARRANGE_ARRAY (). }
    INTEGER  FUZZY_TIME_COMP          = MAX_TIME;         { set the comparator to a maximum value }
    BYTE     CRITICAL_FLAG            = 0;                { initialize critical flag }
    BYTE     CRITICAL_FLAG_ARRAY [5]  = { 0, 0, 0, 0, 0 };
    BEGIN
        FOR I = 1 TO MAX_PROCESSES
            IF (PROCESS [I].MOVE_FLAG_SET AND FUZZY_TIME [I] < FUZZY_TIME_COMP)
            THEN BEGIN
                TASK_MOVE = I;                                       { finds shortest fuzzy time }
                FUZZY_TIME_COMP = FUZZY_TIME [I];
                IF (FUZZY_TIME = 0) THEN BEGIN
                    SET CRITICAL_FLAG;
                    SET CRITICAL_ARRAY [TASK];
                END;
            END;
        { If two or more processes need to move immediately a rearrangement of earlier
        interleaved tasks occurs to settle conflicts at this point if a fuzzy time range
        settle the conflict the process with the shortest fuzzy time value is set to move. }
        IF CRITICAL_FLAG > 1 THEN REARRANGE_ARRAY ();
            ELSE
            ADD TASK_ARRAY [TASK_MOVE];
    END;
```

TABLE 7

Multitasking (Resource Arbitrate)

```
PROCEDURE RESOURCE_ARBITRATE ()
    { If two or more processes need the same resource (physical location), fuzzy times for the
    processes in question are examined to evaluate whether the time slack can settle the
    conflict. If not, the processes prior tasks are rearranged to circumvent the collision. }
    BYTE   CRITICAL_FLAG            = 0;                 { initialize critical flag }
    BYTE   CRITICAL_FLAG_ARRAY [5]  = { 0, 0, 0, 0, 0 };
    BEGIN
    { Compare process task fuzzy time with other process actual task time. }
        COMPARE CRITICAL_PROCESS_1_FUZZY_TIME WITH
        CRITICAL_PROCESS_2_TASK_TIME;
            IF >TASK_MOVE = PROCESS_2;
        ELSE
        COMPARE CRITICAL_PROCESS_2_FUZZY_TIME WITH
        CRITICAL_PROCESS_1_TASK_TIME;
            IF >TASK_MOVE = PROCESS_1;
        IF TASK_MOVE TRUE
            ADD TASK_ARRAY [TASK_MOVE];
        ELSE BEGIN
```

TABLE 7-continued

Multitasking (Resource Arbitrate)

```
        SET CRITICAL_FLAG;
        SET CRITICAL_FLAG_ARRAY [TASK];
        REARRANGE_TASK_ARRAY ();
    END;
END;
```

TABLE 8

Multitaskinq (Rearrange Tasks)

```
PROCEDURE REARRANGE_TASK_ARRAY ()
    { To prevent conflicts which cannot be arbitrated with fuzzy timing the processes in conflict
    are examined at their previous step(s) and timing adjusted in that task to remedy the
    conflict at the current task. After time adjustment of the critical process the task array
    is reset to the newly adjusted position and returns to the multitask builder and reworks the
    rest of the tasks in all processes. }
    BEGIN
    { Find the last time the critical process was moved. }
        REPEAT
            POSITION = POSITION - 1;
        UNTIL TASK_ARRAY [POSITION] = CRITICAL_FLAG_ARRAY [TASK];
    { Adjust timer. }
        INCREMENT TASK [TASK_ARRAY [POSITION].MIN_TIME] BY X;
    { Reset position and time. }
        SET POSITION TO CURRENT TASK_ARRAY VALUE;
        SET TIMER TO CURRENT TASK_ARRAY VALUE;
        RETURN TO MULTITASK_BUILDER;
    END;
```

It would be clear to one of ordinary skill in the art, after perusal of the specification, drawings and claims herein, that there is a multitude of interleave paths that can be taken to achieve multitasking of a plurality of processes. Each path will in all probability have a different time to complete all of the steps of all of the processes. In view of this it will be appreciated that for optimum efficiency it is necessary to select the optimum path which will take the minimum time to complete. As a practical matter an iterative process can be used in which the interleave path is computed several times. Each time the interleave variables are iterated they are ordered and computed differently so that different results are obtained for each iteration. The number of iterations necessary to arrive at an optimized path can be computed statistically by taking the number of steps in each task and the number of tasks to be performed. Since run time of the paths calculated from the numerous iterations follow a normal distribution curve, the minimum number of iterations necessary to achieve a path that will be among the faster run times can be calculated.

Alternative Embodiments

While preferred embodiments are disclosed herein, many variations are possible which remain within the concept and scope of the invention, and these variations would become clear to one of ordinary skill in the art after perusal of the specification, drawings and claims herein.

We claim:

1. A system for performing a plurality of independent analysis procedures simultaneously, each said procedure having a sample and at least one process step for operating on that sample, said system comprising a robotic arm for moving the samples among a plurality of processing stations; and a processor for selecting, at a plurality of times, a sample to be moved, and for directing said robotic arm to move said sample to be moved; said processor having, means for directing said robotic arm to interleave the process steps of said plurality of independent analysis procedures, a display screen, means for identifying a symbol shown on said display screen in response to a selection from an operator, means for associating a process step with said symbol, and means for recording an ordered sequence of said process steps.

2. A system as in claim 1, wherein said processing stations are disposed in a set of grid locations, and wherein said system comprises a bench robot with a rotatable tower and with sufficient degrees of freedom that it is able to reach each of the grid locations with suitable movement.

3. A system as in claim 1, wherein said processing stations comprise workstations for performing individual steps of the analysis procedures.

4. A system as in claim 1, wherein at least one said processing station comprises one of the group: a bioassay workstation, a biomedical workstation, a chemical process workstation.

5. A system as in claim 1, wherein said processor comprises a memory for storing a start time and an end time for each said process step.

6. A system as in claim 1, wherein said processor comprises a memory for storing timing information for each said process step, said timing information comprising a range of times at which said process step may be in a predetermined state.

7. A system as in claim 1, wherein said processor comprises means for selecting said sample to be moved in response to timing information about said procedures.

8. A system as in claim 1, wherein said processor comprises a memory for storing timing information for each said process step, said timing information comprising a range of times at which said process step may be in a predetermined state; and means for determining an exact time to start each said process step in a first said procedure in response to timing information for at least one process step in a second said procedure.

9. A system as in claim 8, wherein said means for determining comprises means for generating a possible sequence of process steps;

means for examining said possible sequence for possible conflicts; and means for altering said possible sequence in response to said timing information and said possible conflicts.

10. A system as in claim 8, wherein said means for determining comprises means for generating a possible sequence of process steps;

means for examining said possible sequence for timing conflicts occurring before a known time value;

means for advancing said known time value from a beginning of said possible sequence to an end of said possible sequence;

means, when a first process step is found to have a timing conflict with a second process step and said first process step has a range of times at which it may be started, for selecting an exact time to start said first process step; and means, when a first process step is found to have a timing conflict with a second process step and said first and second process steps have exact times at which they may be started, for backtracking said known time value and altering said possible sequence starting from said backtracked known time value to avoid said timing conflict.

11. A system as in claim 8, wherein said processor comprises means for generating a plurality of possible sequences of process steps;

means for evaluating each said possible sequence for total expected time; and means for selecting one said possible sequence with a desired total expected time, so as to minimize a total time required to complete said procedures.

12. A system as in claim 1, wherein said means for identifying comprises a pointing device.

13. A system as in claim 1, comprising means for receiving information from said operator about the process step associated with said symbol.

14. A robotic system to transport a plurality of samples, each sample undergoing a test procedure having a plurality of steps, to a plurality of work stations each associated with one of said steps wherein said samples are undergoing said test procedures substantially simultaneously comprising:

a. a multi axis robotic device means having a predetermined working range area, b. a work table coextensive with said working range area, c. a plurality of work modules having defined physical dimensions and each associated with one of said steps disposed at identifiable locations on said work table, d. computer means for controlling said robotic device, e. means for inputting to said computer the physical dimensions and location on said work table of said work modules, f. means for inputting to said computer a sequence of said steps associated with each of said tests, each of said steps having a time of performance during which said sample must be located at the step's associated work station, said performance being completed at a step end time, g. means associated with said robotic means for coupling to a sample and capable of holding said sample during transportation between steps, h. means for scheduling said robotic device to move a sample sequentially to the work stations associated with the test said sample is undergoing and deposit said sample at said work station until said step end time is reached, i. means for scheduling the movement of each sample after the first step in the test so that it occurs while the other samples are disposed in their work stations, j. means for causing said robotic device to transport said samples responsive to said end times; and k. means for optimizing the scheduling of said device, said means for optimizing including iteration means to produce multiple different schedules, means for providing statistical information concerning the time distribution such iteration should result in, and means for halting said iteration and accepting one of the schedules that comes close to the optimum schedule based on said statistical distribution.

15. Computer means to control the scheduling of multiple tests, each comprising several distinct steps, each step having a starting time and a completion time associated therewith comprising:

a. means for determining a starting time and completion time for each of the steps in the multiple tests, b. means for scheduling the steps of said multiple tests in a single time sequence arrangement interleaving the steps of said tests, c. means for detecting time conflicts of interfering starting and completion times of said interleaved steps, d. means for resolving said time conflicts by adjusting the starting and completion times of one or more of said steps, e. means for displaying information on a display screen, f. means for identifying a symbol shown on said display screen in response to a selection from an operator, g. means for associating a process step with said symbol, and h. means for recording an ordered sequence of said process step.

* * * * *